United States Patent
Tadokoro et al.

(10) Patent No.: US 10,156,740 B2
(45) Date of Patent: Dec. 18, 2018

(54) SPECTACLE WEARING PARAMETER MEASUREMENT DEVICE, SPECTACLE WEARING PARAMETER MEASUREMENT PROGRAM, AND POSITION SPECIFYING METHOD

(71) Applicant: HOYA LENS THAILAND LTD., Patumthani (TH)

(72) Inventors: Nobuyuki Tadokoro, Tokyo (JP); Naoya Hirono, Tokyo (JP); Masaaki Matsushima, Tokyo (JP)

(73) Assignee: HOYA LENS THAILAND LTD., Patumthani (TH)

( * ) Notice: Subject to any disclaimer, the term of this patent is extended or adjusted under 35 U.S.C. 154(b) by 0 days.

(21) Appl. No.: 15/547,898

(22) PCT Filed: Mar. 10, 2016

(86) PCT No.: PCT/JP2016/057609
§ 371 (c)(1),
(2) Date: Aug. 1, 2017

(87) PCT Pub. No.: WO2016/143862
PCT Pub. Date: Sep. 15, 2016

(65) Prior Publication Data
US 2018/0024384 A1    Jan. 25, 2018

(30) Foreign Application Priority Data
Mar. 10, 2015  (JP) .................. 2015-047760

(51) Int. Cl.
G02C 13/00    (2006.01)
A61B 3/11     (2006.01)
(Continued)

(52) U.S. Cl.
CPC .......... *G02C 13/003* (2013.01); *A61B 3/0041* (2013.01); *A61B 3/11* (2013.01);
(Continued)

(58) Field of Classification Search
CPC .... G02C 13/005; G02C 13/003; G02C 7/027; A61B 3/111; A61B 3/0025
(Continued)

(56) References Cited

U.S. PATENT DOCUMENTS 5,257,721 A    11/1993  Smith et al.
6,533,418 B1    3/2003  Izumitani et al.
(Continued)

FOREIGN PATENT DOCUMENTS

FR    2931001 A1      11/2009
JP    2003-030296 A    1/2003
(Continued)

OTHER PUBLICATIONS

Jun. 7, 2016 International Search Report issued in Patent Application No. PCT/JP2016/057609.
(Continued)

*Primary Examiner* — Mohammed Hasan
(74) *Attorney, Agent, or Firm* — Oliff PLC

(57) ABSTRACT

A spectacle wearing parameter measurement device used in measurement of a spectacle wearing parameter of a subject who is to wear a spectacle frame, the spectacle wearing parameter measurement device includes: an information processing unit that acquires each of a first image as a face image of the subject in a spectacle-frame wearing state and a second image as a face image in a spectacle-frame non-wearing state and prepares a third image obtained by associating the first image and the second image; a display screen unit that displays the third image prepared by the information processing unit; an operation unit that specifies a
(Continued)

measurement reference point of the spectacle wearing parameter on the third image displayed on the display screen unit; and a measurement computation section that calculates the spectacle wearing parameter by using data of the specified measurement reference point.

6 Claims, 8 Drawing Sheets

(51) Int. Cl.
*G01B 11/26* (2006.01)
*G01B 11/00* (2006.01)
*G01B 11/02* (2006.01)
*A61B 3/00* (2006.01)
*G06T 7/00* (2017.01)

(52) U.S. Cl.
CPC .............. *G01B 11/00* (2013.01); *G01B 11/02* (2013.01); *G01B 11/26* (2013.01); *G02C 13/00* (2013.01); *G06T 7/0014* (2013.01); *G06T 2207/20221* (2013.01); *G06T 2207/30041* (2013.01)

(58) Field of Classification Search
USPC ........................................................ 351/204
See application file for complete search history.

(56) References Cited

U.S. PATENT DOCUMENTS

| | | |
|---|---|---|
| 7,845,797 B2 | 12/2010 | Warden et al. |
| 2014/0168599 A1 | 6/2014 | Vossoughi et al. |
| 2018/0031868 A1* | 2/2018 | Tadokoro ............... G01B 11/26 |

FOREIGN PATENT DOCUMENTS

| | | |
|---|---|---|
| JP | 2006-155638 A | 6/2006 |
| JP | 2007-216049 A | 8/2007 |
| JP | 3976925 B2 | 9/2007 |
| JP | 2014-513328 A | 5/2014 |

OTHER PUBLICATIONS

Jul. 19, 2018 Extended Search Report issued in European Patent Application No. 16761828.9.

* cited by examiner

SPECTACLE WEARING PARAMETER MEASUREMENT DEVICE, SPECTACLE WEARING PARAMETER MEASUREMENT PROGRAM, AND POSITION SPECIFYING METHOD

TECHNICAL FIELD

The present invention relates to a spectacle wearing parameter measurement device, a spectacle wearing parameter measurement program, and a position specifying method used when spectacle wearing parameters are to be measured.

BACKGROUND ART

Generally, for preparing spectacle lenses, spectacle wearing parameters measured in a state in which a spectacle wearer is wearing a spectacle frame are required. As the spectacle wearing parameters, a corneal vertex distance, a frame forward-tilt angle, a fitting-point position, an interpupillary distance, a frame warp angle, etc. are known.

Measurement of the spectacle wearing parameters is performed by using a dedicated measuring device. Examples of the dedicated measuring device include a device configured to image the face of a subject in a spectacle-frame wearing state and compute and obtain various spectacle wearing parameters based on the face images, which are imaging results thereof (for example, see Patent Literature 1). Specifically, in the measuring device disclosed in Patent Literature 1, the imaging result of the face of the subject is displayed on a screen, a point serving as a reference for measurement (for example, a corneal vertex of the subject, a spectacle-frame front frame, or the like) is specified while a cursor mark or the like is utilized on the screen, and, then, the spectacle wearing parameters such as the corneal vertex distance and the frame forward-tilt angle are computed and obtained based on the position of the measurement reference point on the screen (for example, see the description of paragraphs "0033" to "0035" of Patent Literature 1).

Meanwhile, in order to change the relative positions between the eye position of a spectacle wearer and a spectacle lens, a deformation mechanism is sometimes provided for temples of the spectacle frame. In that case, the temple width is widened with respect to the spectacle frame (for example, see FIG. 1A and FIGS. 2 to 3 of Patent Literature 2).

CITATION LIST

Patent Literature

Patent Literature 1: JP 3976925 B2
Patent Literature 2: JP 2014-513328 A

SUMMARY OF INVENTION

Technical Problem

As described above, the measurement of the spectacle wearing parameters is performed based on the position of the measurement reference point on the screen. In other words, the specifying of the position of the measurement reference point on the screen displaying the face image of the subject is essential processing for measuring the spectacle wearing parameters. Therefore, the specifying of the position of the measurement reference point is desired to be easily performed. In addition, since the position of the measurement reference point directly affects the measurement results of the spectacle wearing parameters, the specifying thereof is required to be performed with high accuracy. For example, in a case in which the corneal vertex distance is to be measured, the position of the measurement reference point is required to properly match, for example, the corneal vertex of the subject.

However, with the conventional technique, it is not always possible to specify the position of the measurement reference point simply and highly accurately for the reasons described below. The position of the measurement reference point is specified on the screen displaying the face image of the subject. For example, in a case in which the corneal vertex distance is to be measured as the spectacle wearing parameter, the position of the corneal vertex of the subject is specified as one of the measurement reference point on the face image obtained by imaging a lateral side of the face of the subject. However, the image used for measurement of the spectacle wearing parameter and for specifying the position of the spectacle wearing parameter therefor is obtained by imaging the face of the subject wearing the spectacle frame. Therefore, depending on the shape of the spectacle frame worn by the subject, a part that is difficult to see with respect to the face of the subject is generated, and the position of the measurement reference point to be specified may become unclear. Specifically, for example, spectacle frames of a plastic-based material include those having a large temple width, and a situation that the corneal vertex of the subject is hidden by the temple of the spectacle frame on the face image may occur. In such a case, there are possibilities that the position of the measurement reference point cannot be easily specified and that necessary and sufficient positional accuracy with respect to the position of the measurement reference point after the specifying cannot be ensured. As described in Patent Literature 2, if a spectacle frame having a large temple width is used, the cornea may be hidden by the spectacle frame so that it is unable to be seen. In such a case, there are possibilities that the position of the measurement reference point cannot be easily specified and that necessary and sufficient positional accuracy with respect to the position of the measurement reference point after the specifying cannot be ensured. Therefore, it may be difficult to measure the distance of the wearing parameters including the corneal vertex.

Therefore, in the measurement of the spectacle wearing parameters, it is an object of the present invention to provide, in a case in which the position of a measurement reference point is to be specified on a face image of a subject, a spectacle wearing parameter measurement device, a spectacle wearing parameter measurement program, and a position specifying method which enable to specify the position of the measurement reference point thereof.

Solution to Problem

The present invention has been devised to achieve the above object.

A first aspect of the present invention is a spectacle wearing parameter measurement device used in measurement of a spectacle wearing parameter of a subject who is to wear a spectacle frame, the spectacle wearing parameter measurement device having: an information processing unit that acquires each of a first image as a face image of the subject in a spectacle-frame wearing state and a second image as a face image in a spectacle-frame non-wearing state and prepares a third image obtained by associating the first image and the second image; a display screen unit that displays the image prepared by the information processing unit; an operation unit that specifies a measurement reference point of the spectacle wearing parameter on the image displayed on the display screen unit; and a computation unit that calculates the spectacle wearing parameter by using data of the specified measurement reference point.

A second aspect of the present invention is the spectacle wearing parameter measurement device according to the first aspect, wherein the third image is a synthetic image obtained by synthesizing the first image in the spectacle-frame wearing state and the second image in the spectacle-frame non-wearing state and includes at least a measurement position.

A third aspect of the present invention is the spectacle wearing parameter measurement device according to the second aspect, wherein the synthetic image is a synthetic image of a partial region of the first image in the spectacle-frame wearing state and a corresponding region of the second image in the spectacle-frame non-wearing state.

A fourth aspect of the present invention is the spectacle wearing parameter measurement device according to the third aspect, wherein the partial region is a region including a rim part of the spectacle frame worn by the subject on the first image obtained by imaging a lateral side of the face of the subject; and the corresponding region is a region not including an eyeball corneal part of the subject on the second image obtained by imaging a lateral side of the face of the subject.

A fifth aspect of the present invention is a non-transitory computer-readable recording medium storing a spectacle wearing parameter measurement program that causes a computer provided with a display screen unit and an operation unit and used in measurement of a spectacle wearing parameter of a subject who is to wear a spectacle frame to function as:

an image processing section that prepares a third image obtained by associating a first image as a face image of the subject in a spectacle-frame wearing state and a second image as a face image in a spectacle-frame non-wearing state; a display control section that displays the third image by the display screen unit, the third image prepared by the image processing section; an operation control section that causes the operation unit to specify a measurement reference point of the spectacle wearing parameter on the third image displayed on the display screen unit; and a measurement computation section that calculates the spectacle wearing parameter by using data of the specified measurement reference point.

A sixth aspect of the present invention is a position specifying method for specifying, when a spectacle wearing parameter about a subject is to be measured by using a face image of the subject in a wearing state of a spectacle frame, a measurement reference point on the face image required for the measurement; the position specifying method including: acquiring each of a first image as the face image of the subject in a spectacle-frame wearing state and a second image as the face image in a spectacle-frame non-wearing state; when the measurement reference point is to be specified, preparing and displaying a third image obtained by associating the first image in the spectacle-frame wearing state and the second image in the spectacle-frame non-wearing state; and specifying the measurement reference point of the spectacle wearing parameter on the third image.

Advantageous Effects of Invention

According to the present invention, in a case in which the position of the measurement reference point is to be specified on the face image of the subject for measurement of the spectacle wearing parameters, the position of the measurement reference point can be specified.

DESCRIPTION OF EMBODIMENTS

Figure 1A:
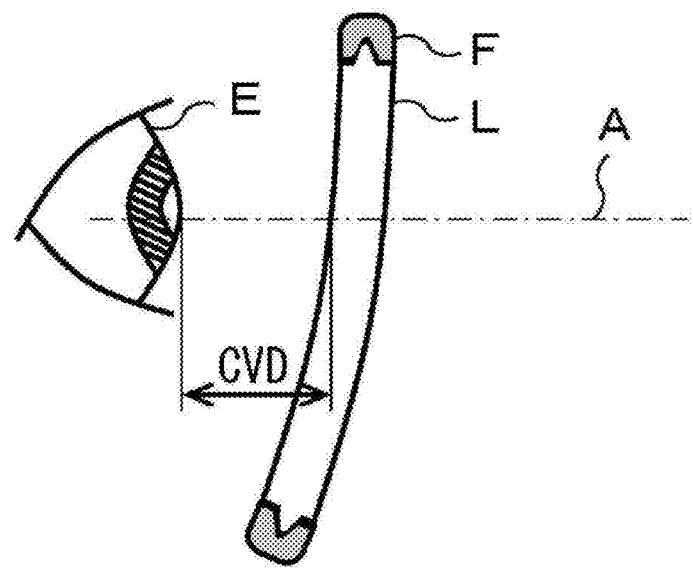
FIG. 1A and FIG. 1B are explanatory views showing specific examples of spectacle wearing parameters.

Hereinafter, embodiments of the present invention will be described with reference to the drawings.

Here, description will be given with the following item classification.
1. Outlines of the Present Invention
2. Specific Examples of Spectacle wearing Parameters
3. Configuration Example of Spectacle wearing parameter measurement device
4. Procedure of Spectacle wearing parameter measurement Method
4-1. Outline of Procedures
4-2. Details of Characteristic Procedures
4-3. Other Procedures
5. Effects of Present Embodiment
6. Modification Examples, etc.

6-1. Modification Examples of Synthetic Image
6-2. Application to Those Other Than Images of Lateral Side of Face
6-3. Use of Measurement Supporting Tool 1. Outlines of the Present Invention First, the outlines of the present invention will be described.

The present invention is used for measuring spectacle wearing parameters. More specifically, the face of a subject wearing a spectacle frame is imaged, a face image which is as an imaging result thereof is displayed on a screen, a point (for example, a corneal vertex of the subject, a spectacle-frame front frame, etc.) which is a reference of measurement on the face image is specified, and, then, various spectacle wearing parameters are computed and obtained based on the positions of the measurement reference points, thereby measuring the spectacle wearing parameters.

In the present invention, such measurement of the spectacle wearing parameters is performed by using a spectacle wearing parameter measurement device, wherein a device body (housing) is configured to be portable. This is for a reason that, if it is portable, installation space like that of a non-portable large-scale measuring device is not required, and introduction to eyewear shops can be facilitated.

The configuration of the portable spectacle wearing parameter measurement device is not particularly limited as long as the device can be carried by hand by a measurer (that is, the examiner for the subject) of the spectacle wearing parameters. For example, it is conceivable to use a portable tablet terminal device which is a computer having an imaging function, an image display function, an operation function, and an information processing function. When the tablet terminal device is used, an imaging function, an image display function, an operation function, and an information processing function necessary and sufficient for measuring the spectacle wearing parameters are obtained, and the tablet terminal devices have been widely spread in recent years. In view of that, the portable spectacle wearing parameter measurement device can be realized at low cost, and it can be said that it is very suitable for promoting introduction to eyewear shops.

By the way, for example, a portable tablet terminal device generally adopts a touch interface in which an operator touches and directly operates an operation target. By virtue of this, simple operability can be realized. However, in a case in which such a tablet terminal device is used as a spectacle wearing parameter measurement device, the face image obtained by imaging the face of the subject in a spectacle-frame wearing state is displayed and used as an operation target. Therefore, as already described, it is conceivable that, depending on the shape of the spectacle frame worn by the subject, a part which is difficult to see with respect to the face of the subject is generated, and operability is deteriorated by this. Regarding this point, the inventors of the present application have carried out intensive studies. As a result, the inventors of the present application conceived that, if a face image of a subject in a non-wearing state of a spectacle frame is also displayed so that an examiner (operator) can perceive it while displaying a face image of the subject in a wearing state of the spectacle frame, generation of the part which is difficult to see with respect to the face of the subject can be avoided, and deterioration of operability caused by that can be suppressed.

In order to realize this, the inventors of the present application further carried out intensive studies. Also, the inventors of the present invention have gotten a completely new idea, which was not present in the past, that a state without a spectacle frame can be easily perceived also at the part which is difficult to see because of the spectacle frame by preparing an imaging result of the face of the subject in a spectacle-frame non-wearing state in addition to an imaging result of the face of the subject in a spectacle-frame wearing state and displaying these imaging results associated with each other in one display screen.

The present invention has been accomplished based on the above-described new idea by the inventors of the present application.

That is, the present invention is characterized by acquiring each of a face image of a subject in a spectacle-frame wearing state (first image) and a face image in a spectacle-frame non-wearing state (second image); when a measurement reference point to be required for measurement of spectacle wearing parameters is to be specified, generating a (processed) image (third image) in which the face images are associated with each other and displaying the third image in one display screen; and specifying the measurement reference points on the processed image.

By having such a characteristic, in a case in which the position of the measurement reference point is to be specified on the face image of the subject for measurement of the spectacle wearing parameters, specifying of the position of the measurement reference points can be realized.

2. Specific Examples of Spectacle Wearing Parameters

Here, the spectacle wearing parameters measured by using the spectacle wearing parameter measurement device will be described.

Figure 1B:
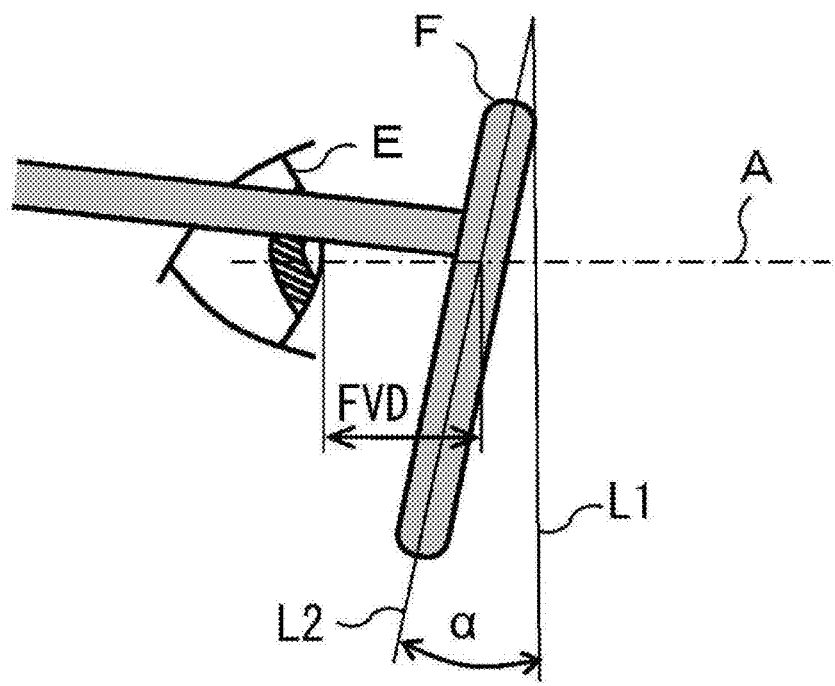

FIG. 1A and FIG. 1B are explanatory views showing specific examples of spectacle wearing parameters.

As the spectacle wearing parameters, for example, a corneal vertex distance and a frame forward-tilt angle in a state in which a subject is wearing a spectacle frame are known.

As shown in FIG. 1A, in a case in which a vision axis of a distant vision of the subject (spectacle wearer) is assumed to be a distant vision axis A, the corneal vertex distance is a distance CVD from the corneal vertex of an eyeball E of the subject on the distant vision axis A to an inner surface of a spectacle lens L framed in a spectacle frame F worn by the subject.

However, the spectacle lens L framed in the spectacle frame F has a different curvature of the inner surface depending on the spherical power, astigmatism power, etc. prescribed for the subject. On the other hand, measurement of the spectacle wearing parameters is generally performed at the timing when the subject is to newly purchase glasses, in other words, in a state in which the subject is wearing a spectacle frame in which sample lenses are framed in at an eyewear shop. Therefore, even if the corneal vertex distance CVD is measured at the eyewear shop, the measurement result thereof does not necessarily reflect the prescribed power, etc. of the subject. In addition, in the state of being framed in the spectacle frame F, the position of the inner surface of the spectacle lens L is often difficult to see.

Therefore, in the present embodiment, instead of the corneal vertex distance CVD, a frame corneal-vertex distance FVD is measured as the spectacle wearing parameter.

As shown in FIG. 1B, the frame corneal-vertex distance FVD in a case in which the vision axis of a distant vision of a subject (spectacle wearer) is a distant vision axis A is the distance obtained by extending a line in this state in a horizontal direction toward a spectacle frame F worn by the subject from the vertex of the cornea of an eyeball E of the subject on the distant vision axis A to the intersection point of the straight line connecting the center of the width of an upper rim at an outer-periphery uppermost end of the spectacle frame F and the center of the width of a lower rim at an outer-periphery lowermost end of the spectacle frame F.

If the spectacle frame F is rimless, the distance to the intersection point with the straight line connecting the upper end of a dummy lens attached to the spectacle frame F and the midpoint of the width of the lower edge is the corneal-vertex frame distance.

Further, if the spectacle frame F is that of a semi-rimless glasses, the distance to the intersection point with the straight line connecting the center of the width of a rim bar or the center of the width of a blow bar and the midpoint of the width of the lower edge of a dummy lens is the corneal-vertex frame distance.

Note that, if the prescribed power, etc. of the spectacle lens L are determined, the corneal vertex distance CVD to which the prescribed power, etc. are reflected can be uniquely derived by performing geometric calculations, etc. based on the measurement result of the frame corneal-vertex distance FVD while using the refractive index of a lens base material, a lens convex-surface curve shape, a lens concave surface curve shape, a lens thickness, a frame forward-tilt angle, a frame warp angle, a lens forward-tilt angle, an eyepoint, and the position of a lens ridge as calculation parameters.

The frame forward-tilt angle generally refers to the angle formed by the rim and a temple of the spectacle frame F. However, in the present embodiment, as shown in FIG. 1B, the frame forward-tilt angle refers to an angle α formed by a straight line (in other words, a straight line extending in a vertical direction) L1 orthogonal to the distant vision axis A and a rim center line L2 of the spectacle frame F.

These spectacle wearing parameters are merely specific examples. In other words, the spectacle wearing parameters are not limited to these, but are only required to include at least one of these and may include other things. Examples of the other things include a fitting point position, an interpupillary distance, a frame warp angle, a near-vision interpupillary distance, an eyeball torsion angle, etc.

In the present embodiment, a case in which the frame corneal-vertex distance FVD and the frame forward-tilt angle α are measured as the spectacle wearing parameters is exemplified and described in detail below.

3. Configuration Example of Spectacle Wearing Parameter Measurement Device

Next, a configuration example of the spectacle wearing parameter measurement device used for measuring the spectacle wearing parameters will be described.

Figure 2A:
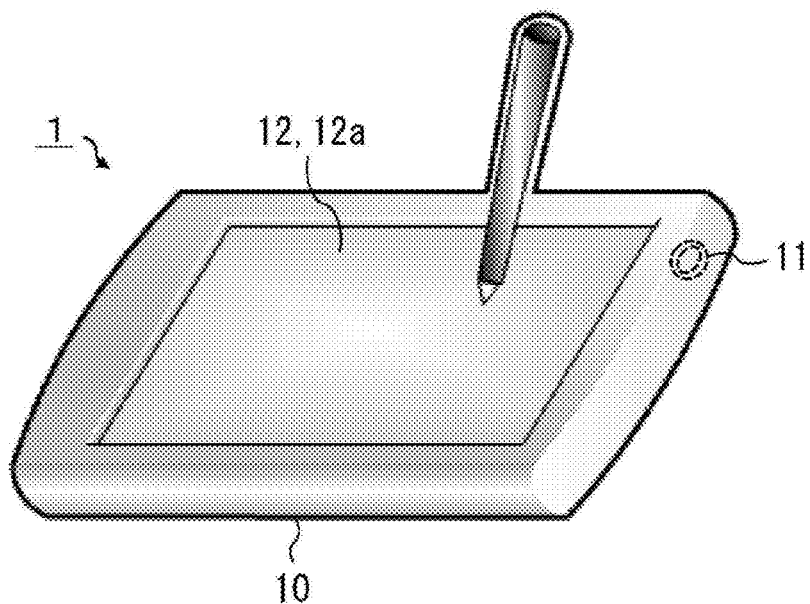
FIG. 2A and FIG. 2B are explanatory views showing a configuration example of a spectacle wearing parameter measurement device according to an embodiment of the present invention.
Figure 2B:
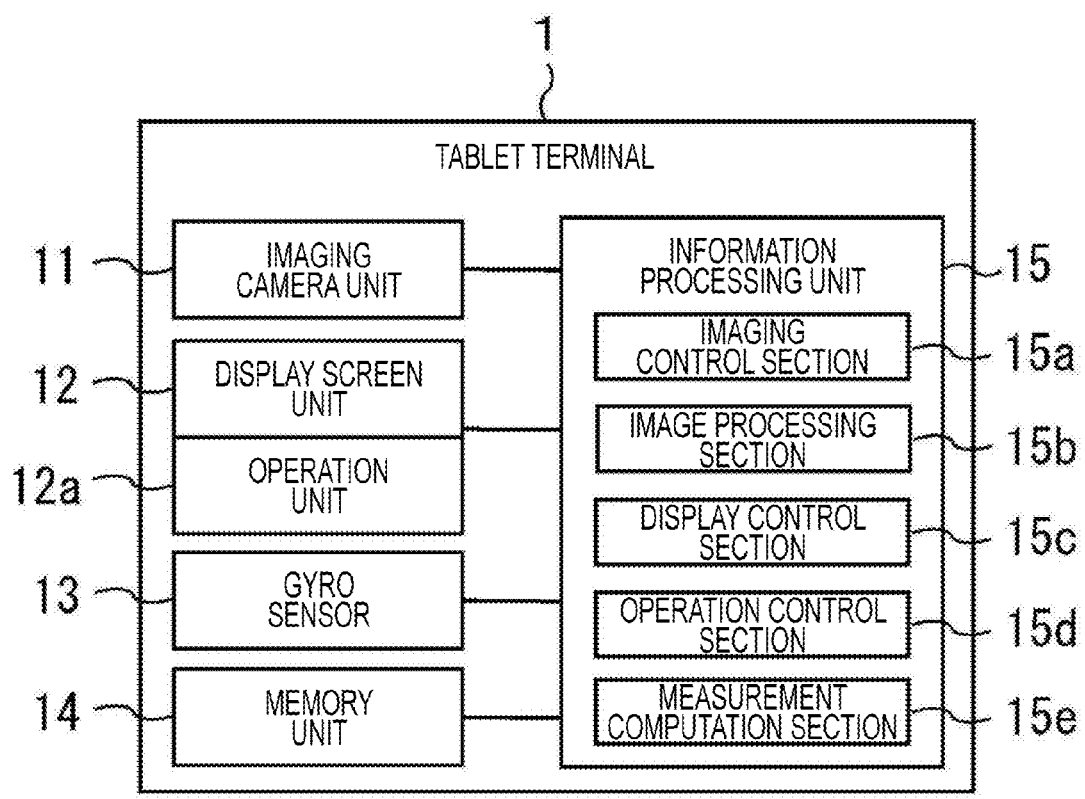

FIG. 2A and FIG. 2B are explanatory views showing the configuration example of the spectacle wearing parameter measurement device according to an embodiment of the present invention; wherein FIG. 2A shows an external perspective view, and FIG. 2B shows a functional block diagram.

As shown in FIG. 2A, the spectacle wearing parameter measurement device 1 described in the present embodiment is formed by using a portable tablet terminal device. Hereinafter, the spectacle wearing parameter measurement device 1 in the present embodiment will be simply referred to as a "tablet terminal".

The tablet terminal 1 is provided with a portable device housing (body) 10 that can be carried by hand by a measurer of the spectacle wearing parameters (that is, an examiner for the subject). The device housing 10 is provided with: an imaging camera unit 11 including a charge coupled device (CCD) sensor or a complementary metal-oxide semiconductor (CMOS) sensor, a display screen unit 12 including a flat panel display such as a liquid crystal display (LCD) panel, and an information processing unit 15 (however, not shown in FIG. 2A) including a central processing unit (CPU). An operation unit 12a, which realizes a touch interface, is attached to the display screen unit 12. The touch interface is a user interface that can be operated by touching the display of the display screen unit 12. With such a touch interface, information from the operation unit 12a can be input to the tablet terminal 1. That is, the tablet terminal 1 functions as a computer having an imaging function, an image display function, an operation function, and an information processing function. The operation of the operation unit 12a with the touch interface may be performed by using a touch pen as shown in the view, but it may be performed directly with the finger(s) of an operator. Furthermore, the operation unit 12a may use information input devices such as a keyboard and a mouse connected to the tablet terminal 1 without using the touch interface.

In addition, as shown in FIG. 2B, in addition to the imaging camera unit 11, the display screen unit 12, the operation unit 12a, the information processing unit 15, the tablet terminal 1 is provided with, in the device housing 10 thereof, a gyro sensor 13 which is a device for detecting the angular velocity and a memory unit 14 composed of a non-volatile memory.

The gyro sensor 13 is used for perceiving the orientation state, etc. of the device housing 10. It should be noted that the one that is originally provided in the tablet terminal 1 may be utilized as the gyro sensor 13.

In the memory unit 14, in addition to the image data obtained by the imaging camera unit 11 and the various data input by the operation unit 12a, a predetermined program required for the processing operation of the information processing unit 15 is stored. When the predetermined program is read and executed from the memory unit 14, the information processing unit 15 functions as an imaging control section 15a, an image processing section 15b, a display control section 15c, an operation control section 15d, and a measurement computation section 15e.

The imaging control section 15a controls the operation of the imaging camera unit 11. The operation control of the imaging camera unit 11 includes controlling whether a shutter is to be operated or not in the imaging camera unit 11. More specifically, the imaging control section 15a permits operation of the shutter only when the orientation of the device housing 10 is in a predetermined state.

Regarding face images of a subject which are imaging results obtained by the imaging camera unit 11, the image processing section 15b performs predetermined image processes on the face images. Specifically, as one of the predetermined image processes, with respect to a first image in a spectacle-frame wearing state of the subject obtained by the imaging camera unit 11 and a second image thereof in a spectacle-frame non-wearing state, the image processing section 15b generates a processed image (third image) associating them. More specifically, as a processed image in which the images are associated, a synthetic image obtained by synthesizing the images is generated. The synthetic image is obtained by performing so-called superimpose synthesis in which, in a partial region of the second image in the spectacle-frame non-wearing state of the subject, the corresponding region of the first image in the spectacle-frame wearing state of the same subject is embedded (both of the regions are synthesized with each other). Examples of the partial region and the corresponding region serving as the targets of the superimpose synthesis include, as described in detail later, a region including an eyeball corneal part of the subject on a face lateral-side image obtained by imaging a lateral side of the face of the subject. That is, in the above example, the synthetic image includes at least a measurement position.

The display control section 15c performs operation control of the display screen unit 12. The operation control of the display screen unit 12 includes control about image contents displayed on the display screen unit 12. Specifically, the display control section 15c causes the display screen unit 12 to display a face image (that is, an image before imaging) of the subject serving as an imaging target by the imaging camera unit 11, thereby causing the display screen unit 12 to function as an imaging finder of the imaging camera unit 11. Furthermore, the display control section 15c causes the display screen unit 12 to perform image display of a face image of the subject (that is, an image obtained by imaging) that is an imaging result of the imaging camera unit 11, thereby subjecting it to the operation by the operation unit 12a to be performed thereafter. At this point of time, as an imaging result by the imaging camera unit 11, the display control section 15c performs image display of the processed image (specifically, for example, superimposed synthetic image), which is generated by the image processing section 15b, by the display screen unit 12.

The operation control section 15d performs operation control of the operation unit 12a. The operation control of the operation unit 12a includes the position recognition of the point specified by the operation unit 12a. Specifically, the operation control section 15d causes the operation unit 12a to specify a point on the face image of the subject displayed on the display screen unit 12, thereby recognizing the position of a measurement reference point, which is necessary for measuring the spectacle wearing parameters, on the displayed image.

The measurement computation section 15e is for obtaining the spectacle wearing parameters about the subject. Specifically, while using the imaging result obtained by the imaging camera unit 11, the measurement computation section 15e performs computation processing of obtaining the spectacle wearing parameters about the subject based on the measurement reference point specified by the operation unit 12a. In the present embodiment, the measurement computation section 15e is also referred to as a computation unit.

Each of these sections 15a to 15e is realized by reading and executing the predetermined program in the memory unit 14 by the information processing unit 15. That is, the functions as the sections 15a to 15e in the tablet terminal 1 are realized by the predetermined program in the memory unit 14 (that is, one embodiment of a spectacle wearing parameter measurement program according to the present invention). In that case, the spectacle wearing parameter measurement program is installed and used in the memory unit 14. However, before the installation, the program may be stored and provided in a storage medium readable by the tablet terminal 1 or may be provided to the tablet terminal 1 through a communication line connected to the tablet terminal 1.

In the present embodiment, the case in which the information processing unit 15 in the device housing 10 functions as the measurement computation section 15e, in other words, the case in which the measurement computation section 15e performs computation processing for obtaining the spectacle wearing parameters in the device housing 10 has been taken as an example. However, for example, if the information processing unit 15 is configured to be able to communicate with a second device on a communication line through the communication line, which is wireless or wired and is connected to the tablet terminal 1, the second device may be configured to have the function of performing computation processing for obtaining the spectacle wearing parameters. That is, the device housing 10 of the tablet terminal 1 is only required to be provided with at least the imaging camera unit 11, the display screen unit 12, and the operation unit 12a, and the function, etc. as the measurement computation section 15e by the information processing unit 15 may be replaced by a second device on a communication line like so-called cloud computing.

4. Procedures of Spectacle Wearing Parameter Measurement Method

Next, procedures of a spectacle wearing parameter measurement method performed by using the tablet terminal 1 having the above-described configuration will be described.
(4-1. Outline of Procedures)

Herein, first, the outline of the procedures of the spectacle wearing parameter measurement method will be described.

Figure 3:
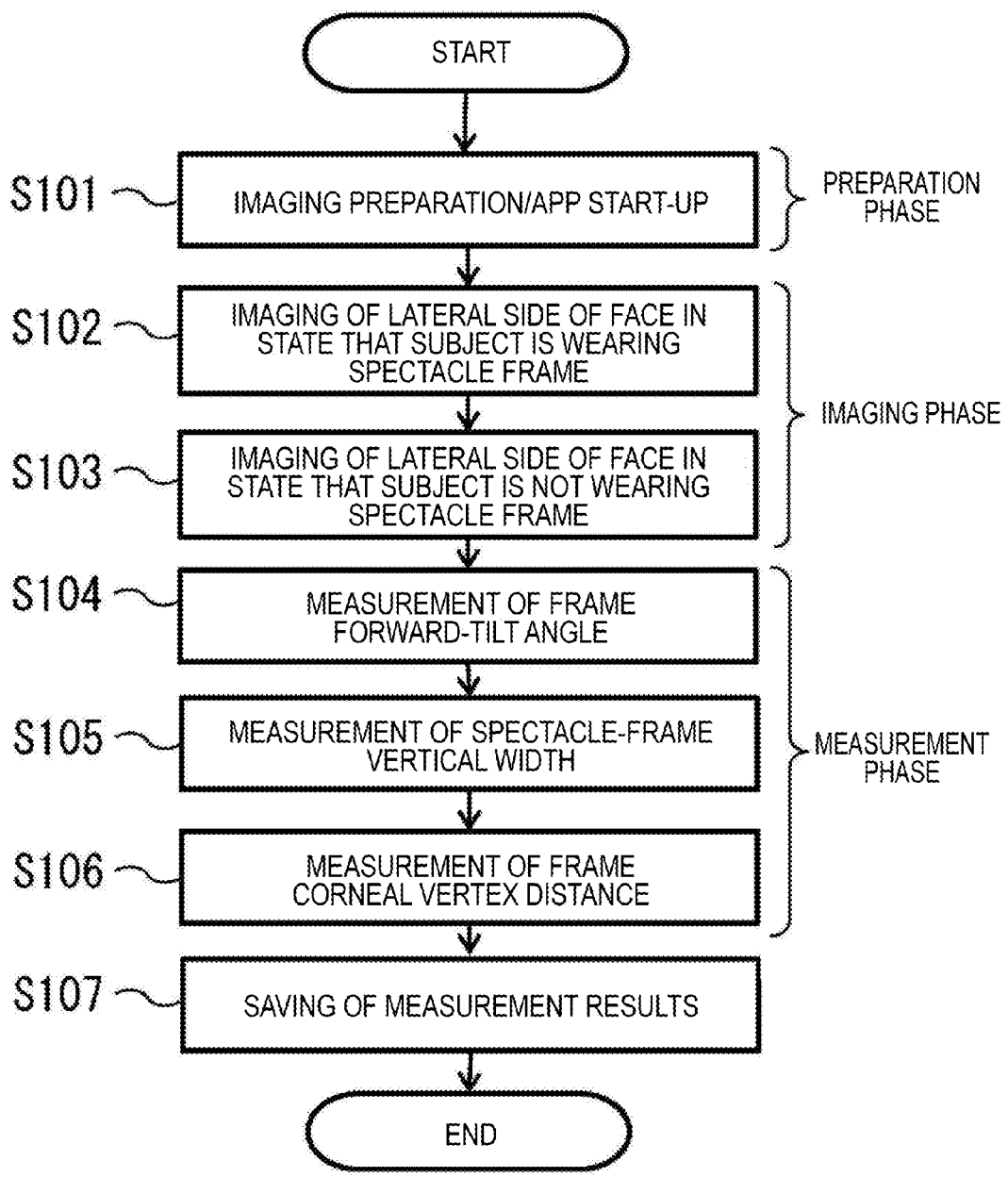
FIG. 3 is a flow chart showing an example of a procedure of a spectacle wearing parameter measurement method according to the embodiment of the present invention.

FIG. 3 is a flow chart showing an example of the procedures of the spectacle wearing parameter measurement method according to the embodiment of the present invention.

In the spectacle wearing parameter measurement method described in the present embodiment, at least a lateral side of the face of the subject in a spectacle-frame wearing state and a lateral side of the face of the subject in a spectacle-frame non-wearing state are imaged, and the frame corneal-vertex distance FVD and the frame forward-tilt angle α are obtained based on the first image (the face image in the spectacle-frame wearing state) and the second image (the face image in the spectacle-frame non-wearing state), which are the imaging results thereof, thereby performing measurement about the spectacle wearing parameters.

Specifically, a measurer of the spectacle wearing parameters (that is, an examiner such as a shop clerk of an eyewear shop) causes a subject of the spectacle wearing parameters (that is, a customer of the eyewear shop or the like) to be prepared for imaging and starts up the tablet terminal 1 in which the spectacle wearing parameter measurement program is installed as an application program (step 101, hereinafter, step will be abbreviated as "S"). At this point of time, the subject prepares a spectacle frame to be worn. Since the portable tablet terminal 1 is used for the imaging of the subject, unlike a case in which a fixed measuring device is used, there is no need to move the subject to an installation site of the device or to cause the subject to take a particular orientation. Up to this point corresponds to the "preparation phase" in the spectacle wearing parameter measurement method of the present embodiment.

After the preparation phase, while the examiner is using the imaging camera unit 11 of the tablet terminal 1 in a state in which the examiner is holding the tablet terminal 1 in his or her hand, the examiner presses a shutter button of the imaging camera unit 11, thereby imaging a lateral side of the face of the subject in the spectacle-frame wearing state (S102) and then imaging the lateral side of the face in the spectacle-frame non-wearing state (S103). As a result, the tablet terminal 1 acquires at least each of the image of the lateral side of the face of the subject in the spectacle-frame wearing state and the image of the lateral side of the face of the subject in the spectacle-frame non-wearing state. Up to this point corresponds to an "imaging phase" in the spectacle wearing parameter measurement method of the present embodiment.

After the imaging phase, the examiner operates the tablet terminal 1 and, at the same time, measures various spectacle wearing parameters based on the imaging result obtained in the imaging phase. Specifically, the tablet terminal 1 obtains, at least, the frame forward-tilt angle α (S104), performs measurement of a frame vertical width of the spectacle frame worn by the subject (S105), and, then, obtains the frame corneal-vertex distance FVD (S106). Up to this point corresponds to a "measurement phase" in the spectacle wearing parameter measurement method of the present embodiment. Then, the tablet terminal 1 saves the measurement results of the various spectacle wearing parameters obtained in this manner, for example, in the memory unit 14 (S107).

In this manner, in the spectacle wearing parameter measurement method described in the present embodiment, in a rough classification, the measurement about the spectacle wearing parameters is performed through the preparation phase, the imaging phase, and the measurement phase. It should be noted that the phases are not necessarily performed in this order, and they may be performed concurrently in parallel. Specifically, for example, after the first image of the subject in the spectacle-frame wearing state is acquired in the imaging phase (S102), the measurement phase may be started to obtain the frame forward-tilt angle α (S104) before the second image in the spectacle-frame non-wearing state is acquired (S102).

(4-2. Details of Characteristic Procedures)

Subsequently, characteristic procedures in the spectacle wearing parameter measurement method that is subjected to the above phases will be described in detail with reference to specific examples.

(S102: Imaging Process of First Image in Spectacle-Frame Wearing State)

Figure 4A:
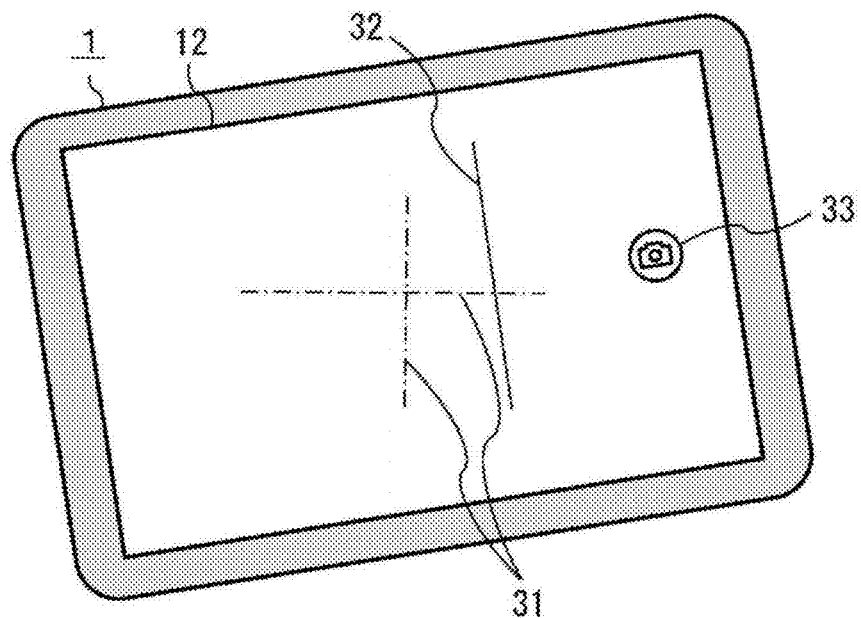
FIG. 4A and FIG. 4B are explanatory views showing specific examples of contents displayed on an imaging finder of the spectacle wearing parameter measurement device according to the embodiment of the present invention and are views showing display contents required when a first image of a subject in the spectacle-frame wearing state is to be obtained by imaging.
Figure 4B:
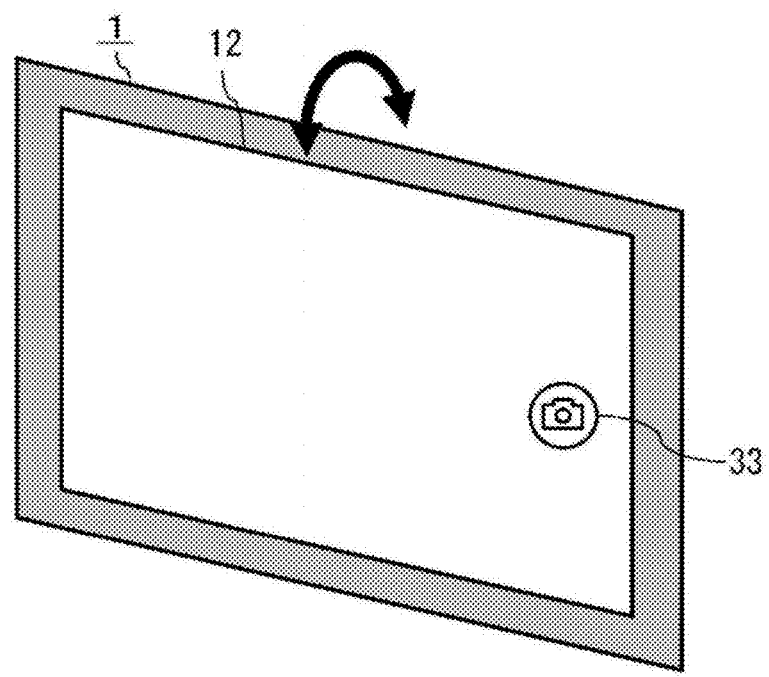
Figure 5A:
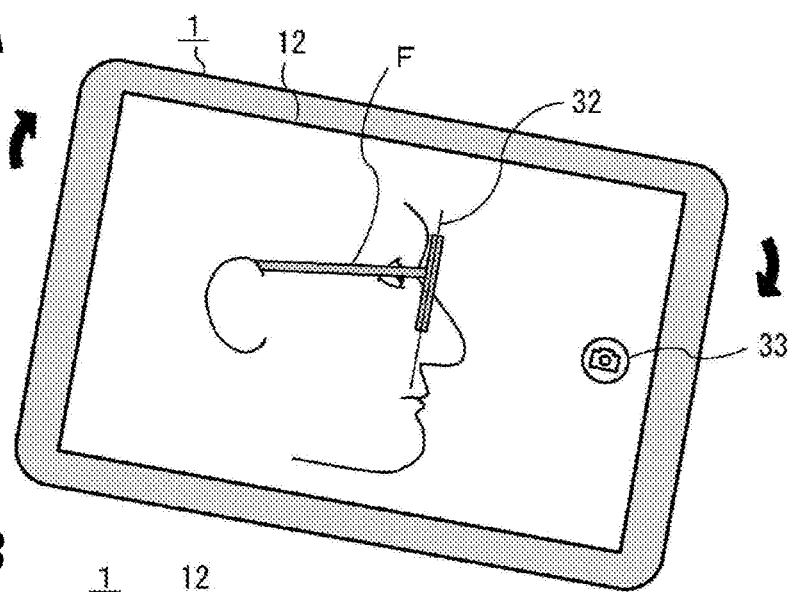
FIG. 5A, FIG. 5B, and FIG. 5C are explanatory views showing specific examples of the contents to be displayed on an imaging finder of the spectacle wearing parameter measurement device in the embodiment of the present invention and are views showing display contents in a case in which a lateral side of the face of the subject is to be imaged.
Figure 5B:
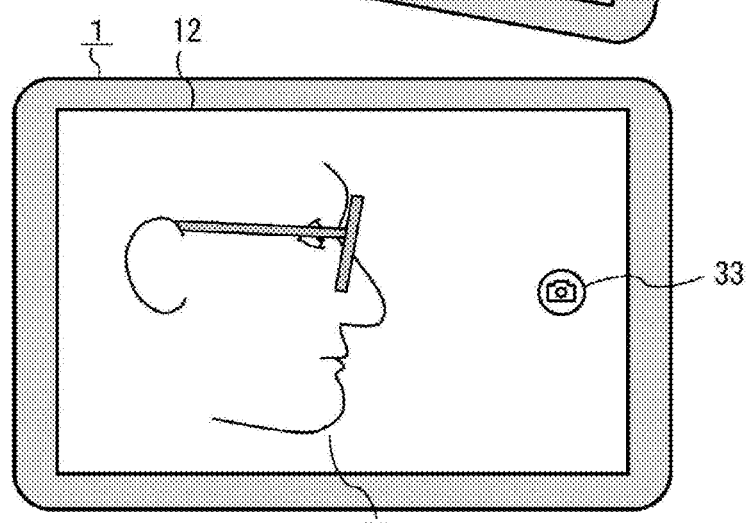
Figure 5C:
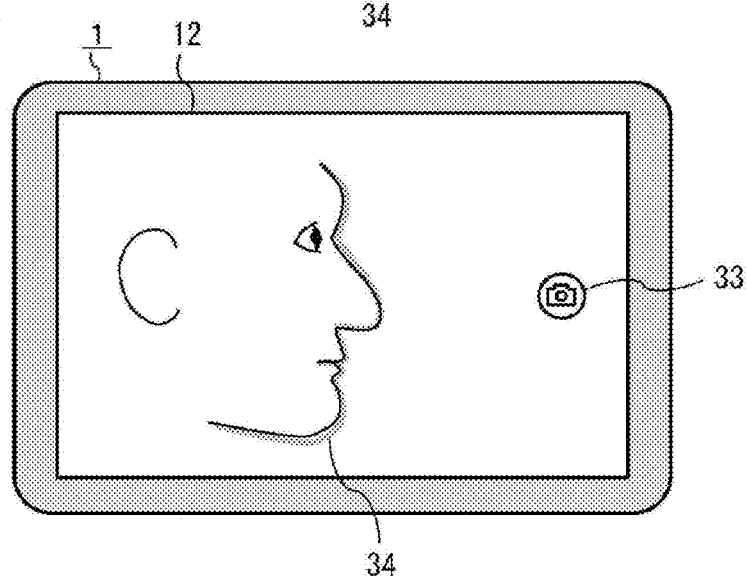

FIG. 4A and FIG. 4B are explanatory views showing specific examples of contents displayed on the imaging finder of the spectacle wearing parameter measurement device according to the embodiment of the present invention and are views showing display contents required when the first image of the subject in the spectacle-frame wearing state is to be obtained by imaging. FIG. 5A, FIG. 5B, and FIG. 5C are explanatory views also showing specific examples of the contents to be displayed on the imaging finder and are views showing the display contents in a case in which a lateral side of the face of the subject is imaged.

When the first image of the subject in the spectacle-frame wearing state is to be obtained by imaging, the tablet terminal 1 first becomes an imaging mode for the spectacle-frame wearing state in response to a predetermined operation by the examiner who performs the imaging.

The tablet terminal 1 which has become the imaging mode for the spectacle-frame wearing state follows control by the display control section 15c; and, at the same time, as shown in FIG. 4A, the tablet terminal 1 displays: first reference lines 31, which include a straight line extending in a vertical direction (in other words, gravity direction) and a straight line extending in the horizontal direction orthogonal thereto; a second reference line 32, which includes a straight line extending in a lengthwise direction of the imaging finder; and a shutter button 33, which is used for imaging, in the imaging finder of the display screen unit 12. As a result, the display screen unit 12 displays the first reference lines 31, the second reference line 32, and the shutter button 33 in addition to the image obtained through the imaging camera unit 11.

The first reference lines 31 are displayed so as to always extend in the vertical direction and the horizontal direction regardless of the state of the orientation of the device housing 10 of the tablet terminal 1. In other words, the first reference lines 31 are always fixedly displayed with respect to the gravity direction regardless of the orientation of the device housing 10. The first reference lines 31 like this can be displayed in the imaging finder by utilizing the function of the gyro sensor 13.

On the other hand, the second reference line 32 is always fixedly displayed with respect to a field angle of the display screen unit 12. Therefore, when the orientation of the device housing 10 of the tablet terminal 1 is changed, the extending direction of the second reference line 32 is also changed in response to that.

Note that, the first reference lines 31 and the second reference line 32 are displayed so that each of them can be distinguished from one another. Specifically, it is conceivable to make them distinguishable by using different display colors, respectively.

The shutter button 33 is pressed by the examiner to perform imaging by the imaging camera unit 11. However, as shown in FIG. 4B, the shutter button 33 is in a pressable state only when the device housing 10 of the tablet terminal 1 is in the orientation in which the device housing 10 is considered to be in an upright state in the vertical direction. Specifically, in a case in which the examiner holds the device housing 10 by hand, if the state in which the device housing 10 is in the upright orientation in the vertical direction is 90°, the shutter button 33 is in the pressable state only when the tilt thereof in a front-rear direction (the direction of an arrow in the view) is, for example, within ±5. Such pressing restriction of the shutter button 33 can be also realized by utilizing the function of the gyro sensor 13.

When the first reference lines 31, the second reference line 32, and the shutter button 33 are displayed in the imaging finder, the examiner sets a lateral side of the face of the subject in the spectacle-frame wearing state as an imaging target of the imaging camera unit 11. Specifically, the examiner causes the subject to wear the spectacle frame, then holds the tablet terminal 1 by hand so as to be opposed to the lateral side of the face of the subject in the spectacle-frame wearing state, and displays the lateral side of the face of the subject in the imaging finder of the display screen unit 12 of the tablet terminal 1.

Then, as shown in FIG. 5A, the examiner adjusts the position at which the tablet terminal 1 is held by moving it in a rotation direction (the direction of arrows in the view) so that the second reference line 32 displayed in the imaging finder matches a rim center line of the spectacle frame F worn by the subject. At this point, the tablet terminal 1 may give guidance to the examiner so as to match the second reference line 32 and the rim center line. It is conceivable to perform the guidance by, for example, displaying character information on the display screen unit 12 by the imaging control section 15a. However, the guidance is not limited thereto, but may be performed by audio output.

If the shutter button 33 becomes the pressable state in the state in which the second reference line 32 is matching the rim center line, the examiner presses the shutter button 33 in this state. When the shutter button 33 is pressed, in the tablet terminal 1, the imaging camera unit 11 images the image in the state in which it is displayed in the imaging finder. The image which is an imaging result of the imaging camera unit 11 (in other words, the image of the lateral side of the face of the subject in the spectacle-frame wearing state) is once displayed on the display screen unit 12 together with the position information of the first reference lines 31 and the second reference line 32 on the image.

Herein, the display control section 15c may move the position of the second reference line 32 on the screen displayed on the display screen unit 12 while following the operation contents of the operation unit 12a by the examiner. As a result of this, even after the imaging of the lateral side of the face of the subject in the spectacle-frame wearing state, the position of the second reference line 32 on the image, which is the imaging result thereof, can be finely adjusted by the examiner.

Then, there is no problem as a result of a check by the examiner, the display contents by the display screen unit 12 is subjected to data saving in the memory unit 14 as the imaging result of the first image of the subject in the spectacle-frame wearing state.

As described above, in the imaging of the first image of the subject in the spectacle-frame wearing state, the tablet terminal 1 described in the present embodiment performs the imaging so that the second reference line 32 displayed in the imaging finder matches the rim center line of the spectacle frame F worn by the subject. When imaging is performed in this manner, as details are described later, the frame forward-tilt angle α, which is one of the spectacle wearing parameters, can be obtained by utilizing the position relation of the first reference lines 31 and the second reference line 32.

Note that, the first image of the subject in the spectacle-frame wearing state obtained by the imaging can be displayed and reused by the display screen unit 12 of the tablet terminal 1 by reading the first image from the memory unit 14 after the first image is subjected to data saving into the memory unit 14. In that case, the display control section 15c, which causes the display screen unit 12 to display the image, may cause the image processing section 15b to perform an image editing process of moving the first image in the rotation direction so that the position of the second reference line 32 is overlapped with the position of the first reference line 31. Through such an image editing process, the display screen unit 12 displays the first image of the subject, which is in the spectacle-frame wearing state, in the state in which the position adjustment amount of the movement of the tablet terminal 1 in the rotation direction in the imaging is corrected (in other words, in the state in which the vertical direction and the horizontal direction of the first image are along the end sides constituting the field angle of the display screen unit 12).

(S103: Imaging Process of Second Image in Spectacle-Frame Non-Wearing State)

When the imaging of the first image of the subject in the spectacle-frame wearing state is finished, the tablet terminal 1 then becomes an imaging mode for the spectacle-frame non-wearing state of the subject in response to a predetermined operation by the examiner.

While following control by the display control section 15c, at the same time, the tablet terminal 1, which has become the imaging mode for the spectacle-frame non-wearing state, as shown in FIG. 5B, displays the shutter button 33, which is used for imaging, and a guide image 34, which is corresponding to the imaging result of the first image of the subject in the spectacle-frame wearing state, in the imaging finder by the display screen unit 12. As a result, in addition to the image obtained through the imaging camera unit 11, the shutter button 33 and the guide image 34 are displayed in the display screen unit 12.

The guide image 34 is an image obtained by subjecting the imaging result, which is obtained in the imaging process of the first image in the spectacle-frame wearing state (S102), to a predetermined image editing process by the image processing section 15b. Other than the above-described image editing process of correcting the position adjustment amount, the predetermined image editing processes include an image editing process of adjusting the transparency of the image so that the image becomes semi-transparent. The adjustment of the transparency of the image may be performed by utilizing publicly known techniques. However, specifically, it is conceivable to adjust the transparency within a range of 20% to 40%, preferably about 30%. When the transparency is adjusted in this manner, even in the state in which the guide image 34 is displayed, another image can be seen through the guide image.

When the shutter button 33 and the guide image 34 are displayed in the imaging finder, the examiner sets the lateral side of the face of the subject in the spectacle-frame non-wearing state as an imaging target of the imaging camera unit 11. Specifically, the examiner causes the subject to take off the spectacle frame, which has been worn by the subject, then holds the tablet terminal 1 by hand so as to be opposed to the lateral side of the face of the subject in the spectacle-frame non-wearing state, and displays the lateral side of the face of the subject in the imaging finder of the display screen unit 12 of the tablet terminal 1.

Then, as shown in FIG. 5C, the examiner adjusts the position of holding the tablet terminal 1 so that the outline of the second image in the spectacle-frame non-wearing state displayed in the imaging finder matches the outline of the guide image 34, which is displayed in the imaging finder, through the imaging camera unit 11. At this point, the tablet terminal 1 may give guidance to the examiner so that the outline of the second image in the spectacle-frame non-wearing state matches the guide image 34. It is conceivable to perform the guidance by, for example, displaying character information on the display screen unit 12 by the imaging control section 15a. However, the guidance is not limited thereto, but may be performed by audio output.

If the shutter button 33 becomes the pressable state in the state in which the outline of the second image in the spectacle-frame non-wearing state matches the guide image 34, the examiner presses the shutter button 33 in this state. When the shutter button 33 is pressed, in the tablet terminal 1, the imaging camera unit 11 images the image in the state in which it is displayed in the imaging finder. The image which is the imaging result of the imaging camera unit 11 (in other words, the image of the lateral side of the face of the subject in the spectacle-frame non-wearing state) is once displayed on the display screen unit 12 together with the guide image 34.

Herein, while following the operation contents of the operation unit 12a by the examiner, regarding the image which is the imaging result of the imaging camera unit 11, the display control section 15c may move the position thereof or expand/reduce the size thereof on the screen displayed on the display screen unit 12. As a result of this, even after the imaging of the lateral side of the face of the subject in the spectacle-frame non-wearing state, the second image can be finely adjusted by the examiner so that the outline of the second image, which is the imaging result thereof, completely matches the guide image 34.

Then, there is no problem as a result of a check by the examiner, the display contents by the display screen unit 12 are subjected to data saving in the memory unit 14 as the imaging result of the second image of the subject in the spectacle-frame non-wearing state.

As described above, in the imaging of the second image of the subject in the spectacle-frame non-wearing state, the tablet terminal 1 described in the present embodiment performs the imaging so that the image matches the guide image 34, which is based on the imaging result of the first image of the subject in the spectacle-frame wearing state. When the imaging is performed in this manner, as the second image of the subject in the spectacle-frame non-wearing state, an image having approximately the same location, size, etc. of the image in the field angle as the already-obtained first image of the subject in the spectacle-frame wearing state. Note that, the second image of the subject in the spectacle-frame non-wearing state obtained by the imaging can be displayed and reused by the display screen unit 12 of the tablet terminal 1 by reading the second image from the memory unit 14 after the second image is subjected to data saving into the memory unit 14.

(S104: Measuring Process of Frame Forward-Tilt Angle α)

After the imaging process of the first image of the subject in the spectacle-frame wearing state (S102) is finished, a measuring process of the frame forward-tilt angle α (S104) can be started. When the frame forward-tilt angle α is to be measured, the tablet terminal 1 becomes a forward-tilt-angle measuring mode in response to a predetermined operation by the examiner.

While following the control by the display control section 15c, the tablet terminal 1 which has become the forward-tilt-angle measuring mode reads the first image of the subject in the spectacle-frame wearing state from the memory unit 14 and displays the first image by the display screen unit 12. Then, in the tablet terminal 1, while using the first image of the spectacle-frame wearing state, the measurement computation section 15e performs a computation process of obtaining the frame forward-tilt angle α. Specifically, according to the first image in the spectacle-frame wearing state read from the memory unit 14, the positions of the first reference lines 31 and the second reference line 32 on the image can be specified; therefore, the measurement computation section 15e considers the vertical-direction straight line of the first reference lines 31 as a straight line L1 (see FIG. 1B) for obtaining the frame forward-tilt angle α and considers the second reference line 32 as a straight line L2 (see FIG. 1B) for obtaining the frame forward-tilt angle α. Then, the measurement computation section 15e obtains the angle formed by the straight line L1 and the straight line L2 on the image as the frame forward-tilt angle α.

The frame forward-tilt angle α obtained by the measurement computation section 15e in this manner is displayed in a predetermined window in the screen of the display screen unit 12 while following the control by the display control section 15c. Then, if there is no problem as a result of a check by the examiner, the result of the computation process is subjected to data saving into the memory unit 14.

(S105: Measuring Process of Spectacle-Frame Vertical Width)

Meanwhile, in the measurement phase, the spectacle wearing parameters are computed and obtained based on the face images, which are the imaging results of the face of the subject. Therefore, for example, regarding the spectacle wearing parameter specified by the magnitude of the distance such as the frame corneal-vertex distance FVD, when it is to be obtained by computing, calibration (calibration) of associating the magnitude of the distance on the face image and the magnitude of the actual distance in real space is required.

For this calibration, in the present embodiment, the measuring process (S105) of the spectacle-frame vertical width about the spectacle frame F worn by the subject is performed. When the measuring process of the spectacle-frame vertical width (S105) is to be performed, the tablet terminal 1 becomes a spectacle-frame vertical-width measuring mode.

Figure 6A:
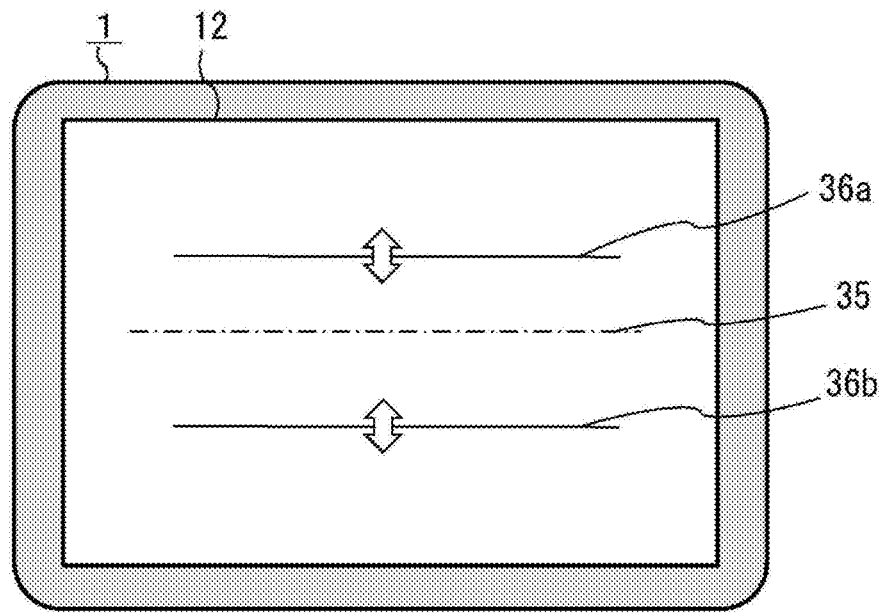
FIG. 6A and FIG. 6B are explanatory views showing specific examples of display contents of a display screen unit in a case in which spectacle wearing parameters are to be obtained by the spectacle wearing parameter measurement device according to the embodiment of the present invention and are views showing display contents in a case in which the frame vertical width of a spectacle frame worn by the subject is to be measured.
Figure 6B:
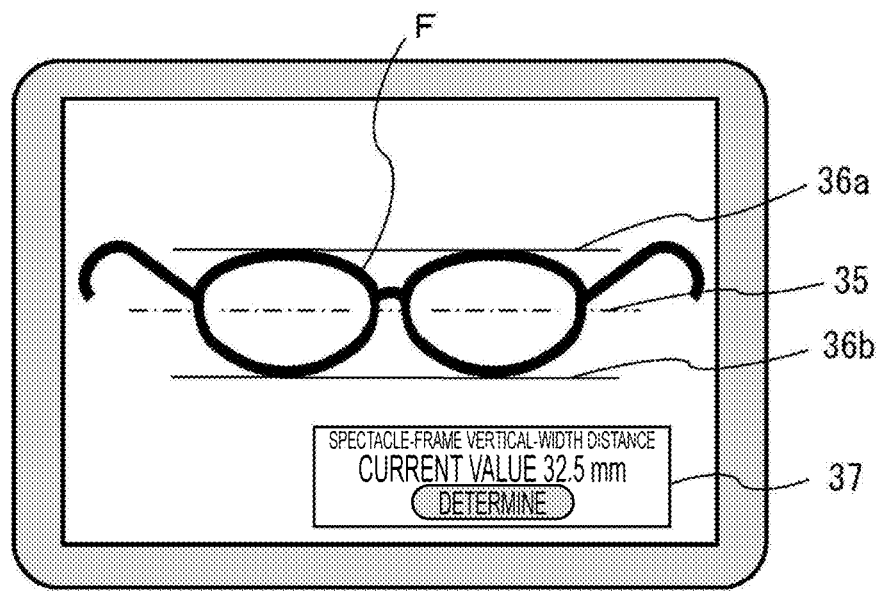

FIG. 6A and FIG. 6B are explanatory views showing specific examples of display contents of the display screen unit in a case in which the spectacle wearing parameters are to be obtained by the spectacle wearing parameter measurement device according to the embodiment of the present invention and are views showing the display contents in a case in which the frame vertical width of the spectacle frame worn by the subject is to be measured.

While following the control by the display control section 15c, as shown in FIG. 6A, the tablet terminal 1 which has become the spectacle-frame vertical-width measuring mode displays a third reference line 35, which consists of a straight line extending along a long side of the screen, and fourth reference lines 36a and 36b, which consist of two straight lines disposed in parallel to the third reference line 35, in the screen of the display screen unit 12.

The third reference line 35 is fixedly displayed in the vicinity of an intermediate point in a top-bottom direction of the screen of the display screen unit 12. The display of the third reference line 35 is not essential, and the display may be omitted.

On the other hand, the fourth reference lines 36a and 36b are displayed so as to sandwich the third reference line 35. Moreover, each of the fourth reference lines 36a and 36b can be independently moved in the screen while the parallel state with the third reference line 35 is maintained. The movement of the fourth reference lines 36a and 36b in the screen is performed while following the operation contents of the operation unit 12a by the examiner.

When the third reference line 35 and the fourth reference lines 36a and 36b are displayed in the screen of the display screen unit 12, as shown in FIG. 6B, the examiner places the spectacle frame F, which is worn by the subject, in a singular state on the screen of the display screen unit 12. At this point, the examiner places the spectacle frame F on the screen so that a datum line of the spectacle frame F matches the third reference line 35. When the third reference line 35 is used in this manner as a guide for placing the spectacle frame F, usability is high for the examiner. Furthermore, when the third reference line 35 is displayed, a screen peripheral region of the display screen unit 12 is not required to be used when the later-described measurement of the spectacle-frame vertical width is to be performed. Therefore, the measurement can be precisely performed.

Subsequently after the spectacle frame F is placed on the screen of the display screen unit 12, the examiner moves the fourth reference lines 36a and 36b in the screen by operating the operation unit 12a. Then, one of the fourth reference lines 36a is caused to match a rim upper end of the spectacle frame F, and the other fourth reference line 36b is caused to match a rim lower end of the spectacle frame F. As a result of this, the interval between the fourth reference lines 36a and 36b matches the magnitude of the frame vertical width of the spectacle frame F.

If a predetermined operation (for example, pressing of an icon image of "determine" which is not shown in the view) by the operation unit 12a is performed in this state, in the tablet terminal 1, the measurement computation section 15e obtains the actual distance between the fourth reference lines 36a and 36b. Specifically, the measurement computation section 15e recognizes the magnitude of the interval between the fourth reference lines 36a and 36b by the number of pixels in the display screen unit 12, obtains the actual distance between the fourth reference lines 36a and 36b by multiplying the recognized number of pixels by the actual magnitude per one pixel, and uses the result of the computation process as the magnitude of the frame vertical width of the spectacle frame F.

The result of the computation process of the frame vertical width obtained by the measurement computation section 15e in this manner is displayed in a predetermined window 37 in the screen of the display screen unit 12 while following the control by the display control section 15c. Then, if there is no problem as a result of a check by the examiner, the result of the computation process is subjected to data saving into the memory unit 14.

In this manner, for the calibration required in the measurement of the spectacle wearing parameters, the tablet terminal 1 described in the present embodiment performs the measuring process (S105) of the spectacle-frame vertical width about the spectacle frame F worn by the subject. Moreover, in the measuring process of the spectacle-frame vertical width (S105), the tablet terminal 1 of the present embodiment converts the magnitude of the frame vertical width of the spectacle frame F to the number of pixels in the display screen unit 12 in the state in which the spectacle frame F is placed on the screen of the display screen unit 12 and then obtains the magnitude of the frame vertical width by a computation process. Therefore, the magnitude of the frame vertical width of the spectacle frame F is not required to be physically measured by a scale or the like, the value of the measurement result thereof is not required to be input to the tablet terminal 1, and the measuring process of the spectacle-frame vertical width (S105) can be easily performed by utilizing the display screen unit 12 of the tablet terminal 1. In addition, there is no need to attach a jig or the like serving as a scale to the spectacle frame F in advance for the calibration required for the measurement of the spectacle wearing parameters. In other words, the series of processes can be completely performed only by the tablet terminal 1, and this is extremely suitable for forming the spectacle wearing parameter measurement device by using the tablet terminal 1.

(S106: Measuring Process of Frame Corneal-Vertex Distance FVD)

After the spectacle wearing parameter measurement device as described above is completed, the measuring process of the frame corneal-vertex distance FVD (S106) can be executed in the tablet terminal 1. When the frame corneal-vertex distance FVD is to be measured, the tablet terminal 1 becomes a frame-corneal-vertex-distance measuring mode in response to a predetermined operation by the examiner.

While following the control by the display control section 15c, the tablet terminal 1, which has become the frame-corneal-vertex-distance measuring mode, reads the imaging results obtained in the imaging processes (S102, S103) from the memory unit 14, displays the imaging results by the display screen unit 12, and subjects them to the operations of the operation unit 12a to be performed by the examiner thereafter. However, at this point, in the tablet terminal 1, the function as the image processing section 15b in the information processing unit 15 performs image processing as described below.

(Image Processing)

FIGS. 7A, 7B, 7C, 7D, and 7E are explanatory views showing specific examples of an image synthesizing process performed by the spectacle wearing parameter measurement device according to the embodiment of the present invention.

Figure 7A:
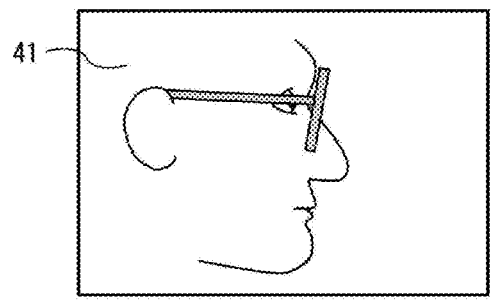
FIGS. 7A, 7B, 7C, 7D, and 7E are explanatory views showing specific examples of an image synthesizing process performed by the spectacle wearing parameter measurement device according to the embodiment of the present invention.
Figure 7B:
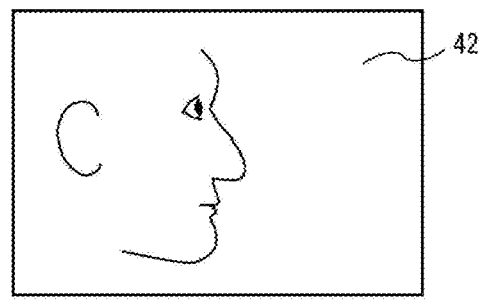

As shown in FIG. 7A, the image processing section 15b reads the first image 41, which is the imaging result about the lateral side of the face of the subject in the spectacle-frame wearing state, from the memory unit 14. Furthermore, as shown in FIG. 7B, the image processing section 15b reads the second image 42, which is the imaging result about the lateral side of the face of the subject in the spectacle-frame non-wearing state, from the memory unit 14.

After the first image 41 in the spectacle-frame wearing state and the second image 42 in the spectacle-frame non-wearing state are read, the image processing section 15b subjects these images 41 and 42 to the image processing required for performing superimpose synthesis.

Figure 7C:
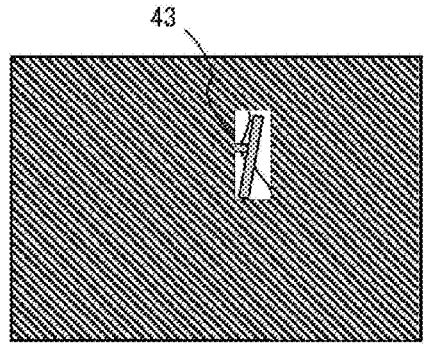

Specifically, as shown in FIG. 7C, the image processing section 15b performs data extraction of a partial region 43 of the first image 41 in the spectacle-frame wearing state and performs data erase of the other region (see hatching part in the view) except for the partial region 43. The position, size, range, etc. of the "partial region" of this case occupied with respect to the entire image are determined in advance, and the "partial region" includes at least the rim part of the spectacle frame F worn by the subject, but is a region set so as not to include a temple part of the spectacle frame F and the eyeball corneal part of the subject. It is conceivable that the partial region 43 has a rectangular shape as shown in the example of the view, but is not limited thereto, and the partial region may be set to a different shape such as a circular shape.

Figure 7D:
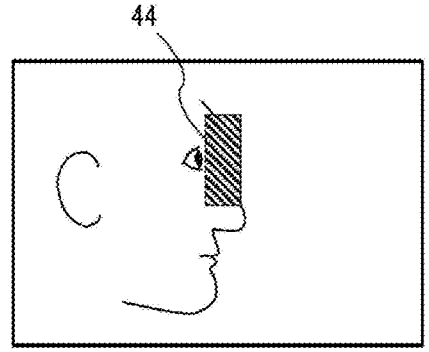

Moreover, as shown in FIG. 7D, the image processing section 15b subjects the face lateral-side image 42 in the spectacle-frame non-wearing state to data erase of a corresponding region 44 corresponding to the above-described partial region 43 (see hatching part in the view). The position, size, range, etc. of the "corresponding region" of this case occupied with respect to the entire image are determined to be the same as those of the partial region 43 so as to correspond to the above-described partial region. Therefore, the corresponding region 44 is also set so as not to include the eyeball corneal part of the subject as well as the above-described partial region 43. The outer shape of the corresponding region 44 may be also any of a rectangular shape, a circular shape, etc. as long as the shape is the same as that of the above-described partial region 43.

It is conceivable that the association between the partial region 43 and the corresponding region 44 is performed based on the position information of the pixels constituting the images 41 and 42. This is for a reason that the first image 41 in the spectacle-frame wearing state and the second image 42 in the spectacle-frame non-wearing state are obtained by imaging so as to have the same view angle and that the location, size, etc. of the image in the field angle are approximately the same except for the presence/absence of the wearing of the spectacle frame. However, the association is not necessarily limited to this, and the partial region 43 and the corresponding region 44 may be associated with each other by another method. Examples of other methods include: subjecting image elements (for example, the ear of the subject, the rim of the spectacle frame) commonly present in the images 41 and 42 to shape recognition, causing the image elements thereof to match each other, and, then, associating the partial region 43 and the corresponding region 44 with each other with high precision based on the position relation with the image elements.

Figure 7E:
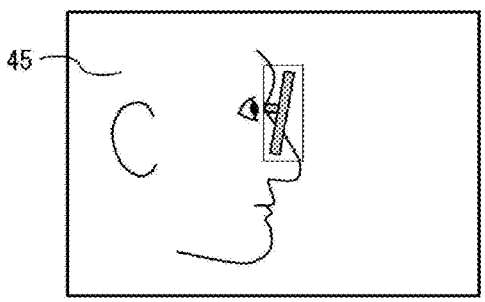

Then, as shown in FIG. 7E, the image processing section 15b subjects these images 41 and 42 to superimpose synthesis so as to embed the partial region 43 in the first image 41 in the spectacle-frame wearing state in the corresponding region 44 in the second image 42 in the spectacle-frame non-wearing state. As a result, the image processing section 15b synthesizes the first image 41 in the spectacle-frame wearing state with the second image 42 in the spectacle-frame non-wearing state to obtain one synthetic image (third image) 45. The synthetic image 45 corresponds to one mode of a processed image in which the images 41 and 42 are associated with each other.

In the single synthetic image 45 obtained by such superimpose synthesis, the partial region 43 in the first image 41 in the spectacle-frame wearing state is replaced by the corresponding region 44 in the second image 42 in the spectacle-frame non-wearing state. Therefore, when such superimpose synthesis is performed, on the single synthetic image 45 obtained as a result thereof, the image part of the spectacle frame is partially deleted in accordance with needs from the synthetic image.

(Specifying Process of Measurement Reference Point)

After the image synthesizing process as described above is performed, in the tablet terminal 1, the single synthetic image 45 obtained by the image synthesizing process is displayed on the display screen unit 12, and, then, the examiner is caused to specify the measurement reference points which are required to measure the frame corneal-vertex distance FVD.

Figure 8A:
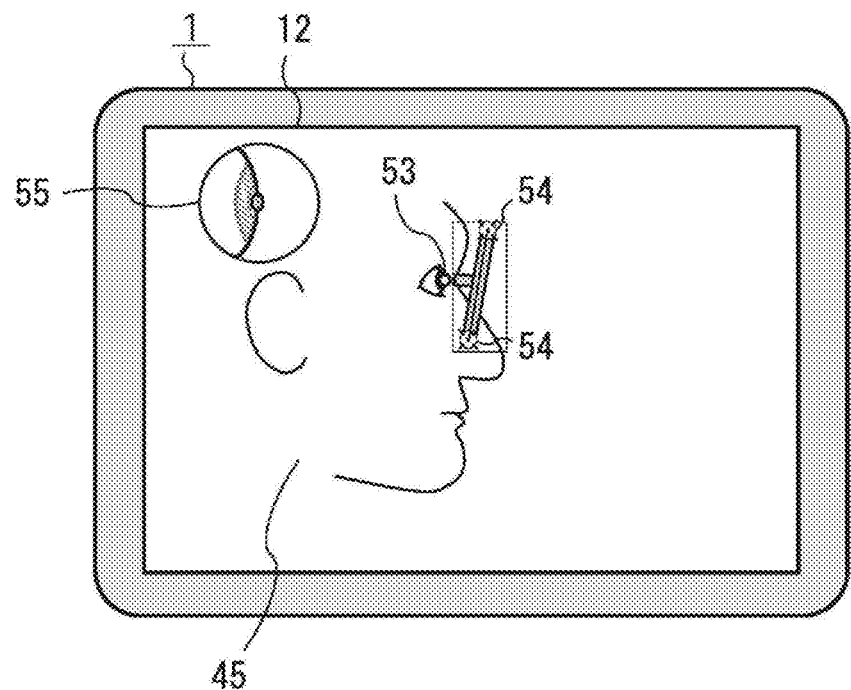
FIG. 8A and FIG. 8B are explanatory views showing specific examples of display contents of the display screen unit in a case in which the spectacle wearing parameters are to be obtained by the spectacle wearing parameter measurement device according to the embodiment of the present invention and are views showing the display contents in a case in which a frame corneal-vertex distance is to be obtained.
Figure 8B:
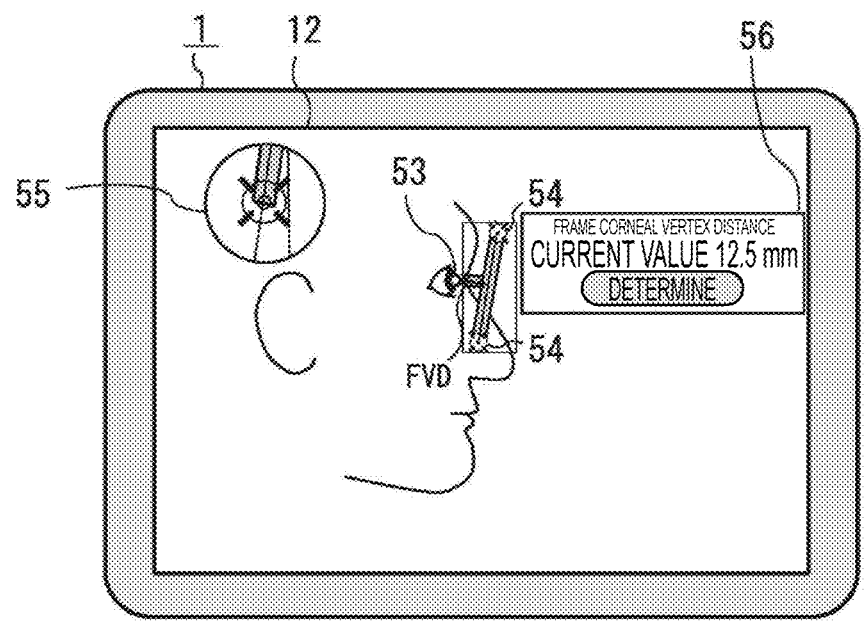

FIG. 8A and FIG. 8B are explanatory views showing specific examples of display contents of the display screen unit in a case in which the spectacle wearing parameters are to be obtained by the spectacle wearing parameter measurement device according to the embodiment of the present invention and are views showing the display contents in a case in which the frame corneal-vertex distance is to be obtained.

Specifically, while following the control by the display control section 15c, as shown in FIG. 8A and FIG. 8B, the tablet terminal 1, which has become the frame-corneal-vertex-distance measuring mode, displays the single synthetic image 45, which has been obtained by the above-described image synthesizing process, by the display screen unit 12, and displays pointer images 53 and 54 in an overlapped manner on the synthetic image 45.

The pointer images 53 and 54 are graphic images which serve as indicators of the position specifying of the points to be specified by the operation unit 12a when specifying of the measurement reference points performed by operating the operation unit 12a is to be performed. Among these, the pointer image 53 is used to specify the position of the corneal vertex in the lateral side of the face of the subject as the measurement reference point. Meanwhile, the pointer images 54 are used when an upper end position and a lower end position of the rim of the spectacle frame F worn by the subject are to be specified as the measurement reference points. The graphic pattern shapes constituting these pointer images 53 and 54 are not particularly limited as long as they are set in advance in consideration of the operability by the examiner and the visibility of the synthetic image 45 to be overlapped.

After the pointer image 53 and 54 are displayed in an overlapped manner on the synthetic image 45, in the tablet terminal 1, as shown in FIG. 8A, the examiner operates the operation unit 12a to position the pointer image 53, which can be moved in the screen of the display screen unit 12, at the vertex of the cornea on the displayed synthetic image 45. At this point, the synthetic image 45 serving as a background is an image from which the image part of the spectacle frame in the face image has been partially deleted in accordance with needs through the superimpose synthesis. Therefore, when the pointer image 53 is to match the position of the corneal vertex, the part at which the vicinity of the cornea of the face of the subject is difficult to be seen is not generated.

Furthermore, in the tablet terminal 1, as shown in FIG. 8B, the examiner operates the operation unit 12a to position the pointer images 54, which can be moved in the screen of the display screen unit 12, at the upper end and the lower end of the rim of the spectacle frame F on the displayed synthetic image 45.

If there is a predetermined operation (for example, pressing of an icon image of "determine") by the operation unit 12a in this state, in the tablet terminal 1, a center point of the pointer image 53 disposed at the position of the corneal vertex is specified as one of the measurement reference points for obtaining the frame corneal-vertex distance FVD, and center points of the pointer images 54 disposed at the upper end and the lower end of the rim of the spectacle frame F are specified as the rest of the measurement reference points for obtaining the frame corneal-vertex distance FVD.

At this point, as shown in FIG. 8A and FIG. 8B, when the examiner touches any of the pointer images 53 and 54 to be moved in the screen, the display control section 15c displays a partially-enlarged window image 55, which displays the pointer image 53 or 54 and a peripheral region thereof in an enlarged manner, at a predetermined part in the screen of the display screen unit 12. By virtue of this, even when the pointer image 53 or 54 is to be moved by operating with the touch interface, the part touched with the touch interface is enlarged and displayed at the predetermined part different from the part by the partially-enlarged window image 55. Therefore, the operability in the positioning by moving the pointer images 53 and 54 by the examiner is improved.

(Computation Process)

When the examiner moves the pointer images 53 and 54 to the respective positions so as to specify the measurement reference points for obtaining the frame corneal-vertex distance FVD, the measurement computation section 15e obtains the intersection point of the straight line extending in the horizontal direction passing through the center of the pointer image 53 positioned at the corneal vertex and the straight line connecting the centers of the pointer images 54 at the upper end and the lower end of the rim of the spectacle frame F. Then, the measurement computation section 15e obtains the distance between the intersection point and the center of the pointer image 53 positioned at the corneal vertex as the frame corneal-vertex distance FVD.

The measurement of the frame corneal-vertex distance FVD in this case is performed on the synthetic image 45 displayed on the display screen unit 12. Therefore, in the measurement of the frame corneal-vertex distance FVD, calibration (calibration) of associating the magnitude in the real space and the magnitude on the synthetic image 45 is required. Since the magnitude of the frame vertical width of the spectacle frame F has been obtained in the above-described measuring process (S105) of the spectacle-frame vertical width, for example, it is conceivable to perform the calibration by associating the result of the computation process of the frame vertical width with the distance between the pointer images 54 disposed at the upper end and the lower end of the rim of the spectacle frame F on the synthetic image 45.

The frame corneal-vertex distance FVD obtained by the measurement computation section 15e in this manner is displayed in a predetermined window 56 in the screen of the display screen unit 12 while following the control by the display control section 15c. Then, if there is no problem as a result of a check by the examiner, the result of the computation process is subjected to data saving into the memory unit 14.

(4-3. Other Procedures)

The characteristic procedures in the measurement of the spectacle wearing parameters in the present embodiment have been described above. However, the tablet terminal 1 may perform other procedures other than the above-described characteristic procedures. Examples of the other procedures include: an imaging process of an upper side of the face of the subject and an imaging process of a front side of the face in the imaging phase, a measuring process of a frame warp angle β in the measuring phase, a measuring process of a fitting-point position FP, and a measuring process of an interpupillary distance PD. Note that, since these procedures may be performed by utilizing publicly known techniques, the detailed description thereof is abbreviated herein.

5. Effects of the Present Embodiment

According to the tablet terminal 1 described in the present embodiment, the spectacle wearing parameter measurement program for realizing the characteristic functions of the tablet terminal 1, and the position specifying method performed by using the tablet terminal 1, following effects are obtained.

According to the present embodiment, the measurement of the various spectacle wearing parameters is performed by utilizing the portable tablet terminal 1. Therefore, installation space like that of a non-portable large-scale measuring device is not required, and introduction to eyewear shops can be facilitated. In this respect, the usability thereof is excellent for the examiner (for example, a clerk of an eyewear shop) who performs the measurement of the various spectacle wearing parameters.

Moreover, in the present embodiment, each of the first image of the subject in the spectacle-frame wearing state and the second image in the spectacle-frame non-wearing state is obtained by imaging, the imaging result about the spectacle-frame wearing state and the imaging result about the spectacle-frame non-wearing state are synthesized and displayed in a single synthetic image, and the measurement reference points required for obtaining the spectacle wearing parameters are specified on the single synthetic image (third image). In other words, in addition to the imaging result of the face image of the subject in the spectacle-frame wearing state, the imaging result of the face image of the subject in the spectacle-frame non-wearing state is prepared, and these imaging results are partially subjected to an image synthesizing process and are displayed as a single synthetic image by the display screen unit 12. Therefore, according to the present embodiment, through the above-described image synthesizing process, the image part of the spectacle frame can be partially deleted in accordance with needs on the single synthetic image after the image synthesizing process. If the image part of the spectacle frame can be partially deleted in this manner, regardless of the shape of the spectacle frame worn by the subject, a situation that it is difficult to see the face of the subject due to the shape of the spectacle frame can be prevented. For example, even if the subject is wearing a spectacle frame having a large temple width, the corneal vertex of the subject can be prevented from being hidden by the temple of the spectacle frame on the face image by deleting the temple part. In other words, according to the present embodiment, when the measurement reference points required for obtaining the spectacle wearing parameters are to be specified, the image part of the spectacle frame is partially deleted in accordance with needs. As a result, obscuring of the positions of the measurement reference points to be specified can be avoided, specifying of the positions of the measurement reference points as a result thereof can be easily performed, and, furthermore, necessary and sufficient position accuracy can be ensured for the specified positions of the measurement reference points.

Particularly, as described in the present embodiment, in the image synthesizing process to the single synthetic image, the partial region of the imaging result about the spectacle-frame wearing state is subjected to the superimpose synthesis of embedding the imaging result about the spectacle-frame non-wearing state in the corresponding region. As a result, only the necessary part (in other words, only the partial region of the imaging result) of the imaging result of the spectacle-frame wearing state can be replaced by the imaging result of the spectacle-frame non-wearing state (in other words, the corresponding region of the imaging result). Therefore, according to the embodiment, only the part required for specifying the measurement reference points is reliably replaced by the face image in the spectacle-frame non-wearing state. In other words, the image part of the spectacle frame not required for specifying the measurement reference points can be reliably deleted, and, as a result, easy and high-precision specifying of the positions of the measurement reference points can be realized.

Incidentally, as a situation in which the positions of the measurement reference points to be specified may be obscured, a case in which the temple of the spectacle frame hides the corneal vertex of the subject on the face image as described above is included as a typical example thereof. Regarding this point, in the present embodiment, the target regions of the superimpose synthesis (in other words, the partial region and the corresponding region) are the regions which are set so as to include at least the rim part of the spectacle frame worn by the subject on the face image obtained by imaging the lateral side of the face of the subject, but so as not to include the temple part of the spectacle frame and the eyeball corneal part of the subject. Therefore, according to the present embodiment, even if the corneal vertex of the subject is hidden by the temple of the spectacle frame on the face image, obscuring of the positions of the measurement reference points to be specified can be avoided. As a result, easy and high-precision specifying of the positions of the measurement reference points required for measuring the frame corneal-vertex distance FVD can be realized. In other words, this is extremely suitable for application to a case in which the frame corneal-vertex distance FVD, which is one of the spectacle wearing parameters, is to be measured.

6. Modification Examples, Etc

The embodiment of the present invention has been described above. However, the above-described disclosed contents show an exemplary embodiment of the present invention. In other words, the technical scope of the present invention is not limited to the above-described exemplary embodiment. Modification examples, etc. will be described below.

(6-1. Modification Examples of Synthetic Image)

In the present embodiment, as the synthetic image (third image) of the first image in the spectacle-frame wearing state and the second image in the spectacle-frame non-wearing state, the case in which the superimpose synthesis image in which the partial region of one of the images is embedded in the corresponding region of the other image is taken as an example. However, the present invention is not limited thereto, and a synthetic image by another synthetic mode may be displayed. Examples of the synthetic image by another synthetic mode include overlapped images in a state in which the transparency thereof is different from each other.

Moreover, as long as the first image in the spectacle-frame wearing state and the second image in the spectacle-frame non-wearing state are displayed in a mutually associated manner, they are not necessarily required to be displayed in a synthesized state. In other words, in the present invention, the processed image (third image), in which the images of the first image in the spectacle-frame wearing state and the second image in the spectacle-frame non-wearing state are mutually associated, may be generated and displayed, and the measurement reference points may be specified on the processed image. The "association" referred to herein is to enable recognition of the relativity of the images when the measurement reference points are to be specified. Therefore, the processed image in which the images are mutually associated includes the following other than the synthetic image described in the present embodiment. Specifically, an example of the processed image is an image processed so as to display the first image in the spectacle-frame wearing state and the second image in the spectacle-frame non-wearing state in a juxtaposed manner and align the positions thereof and/or align the sizes thereof so that the pointer images are synchronously moved at the same positions on the images. The processed image is not limited to the example like this. As long as the first image in the spectacle-frame wearing state and the second image in the spectacle-frame non-wearing state are processed and displayed so as to facilitate viewing of the part required for specifying the measurement reference points regardless of the presence/absence of the spectacle frame, it corresponds to the "processed image (in other words, the third image)" in the present invention. For example, dividing each of the frame-wearing-state and frameless images as described above by a vertical-direction straight line, which is positioned between the corneal vertex and a spectacle front part (the part to which spectacle lenses are attached) and then selecting and juxtaposing the image in the frame wearing state, which is a divided image including the frame front part, and the frameless image, which is a divided image including the corneal vertex, is also a suitable embodiment of the present application. In this case, in the information processing unit 15, rather than newly generating a synthetic image, each of the first image of the subject in the spectacle-frame wearing state and the second image in the spectacle-frame non-wearing state is acquired, and the third image in which the images are mutually associated is prepared.

(6-2. Application to Those Other than Images of Lateral Side of Face)

In the present embodiment, mainly, the processing procedure for measuring the frame corneal-vertex distance FVD is taken as an example. Therefore, in the present embodiment, the case in which the images of the lateral side of the face of the subject are synthesized to generate the synthetic image is described. However, the present invention is not limited thereto, and, other than the lateral side of the face of the subject, it is also conceivable to subject a face upper side, a face front side, etc. of the subject to an image synthesizing process similar to that of the case of the present embodiment. For example, in a sunglasses wearing state, if an eyepoint position on the sunglasses is to be specified, it is not always easy to check the corneal position due to the light-shielding function of the sunglasses. Images are obtained by imaging in a sunglasses wearing state and without the sunglasses, and a synthetic image in which the image including at least the corneal vertex and the image including a frame of the sunglasses are joined is created. As a result, the eyepoint position on the sunglasses can be checked.

(6-3. Use of Measurement Supporting Tool)

In the present embodiment, the case in which, after the measuring process of the spectacle-frame vertical width (S105) is performed, the calibration of associating the magnitude in the real space and the magnitude on the image is performed based on the processing result thereof is taken as an example. However, for example, the calibration may be performed by the examiner by inputting the numerical value of the value of the spectacle-frame vertical width, which has been measured by using a scale or the like, to the tablet terminal 1. Instead of measuring the spectacle-frame vertical width, the calibration may be performed by using a measurement reference scale formed by a graphic having a predetermined size as an index and imaging the index together with a face image of the subject. Specifically, in the imaging phase, a measurement supporting tool on which a measurement reference scale is drawn with a constituting graphic having a known magnitude (in other words, magnitude in real space) serves as an imaging target together with the face of the subject. Then, it is conceivable that, by using any of graphic parts constituting the measurement reference scale included in the imaging result, calibration of associating the magnitude in the real space and the magnitude on the synthetic image of the lateral side of the face is performed so that scale conversion on the synthetic image of the lateral side of the face is performed. The measurement supporting tool may be realized by utilizing publicly known techniques, and detailed description thereof is omitted herein.

(6-4. Image Data)

In the present embodiment, the image data obtained by the imaging camera unit 11 is used. However, image data other than that may be used. For example, instead of the image data obtained by imaging by the imaging camera unit 11 of the tablet terminal 1, image data obtained by imaging the subject by another imaging device may be used. The imaging camera unit 11 is provided in the tablet terminal 1 merely as a preferred example.

REFERENCE SIGNS LIST

1 Spectacle wearing parameter measurement device (tablet terminal)
10 Device housing
11 Imaging camera unit
Display screen unit
12a Operation unit
13 Gyro sensor
14 Memory unit
15 Information processing unit 15a Imaging control section
15b Image synthesizing section
15c Display control section
15d Operation control section
15e Measurement computation section (computation unit)
41 First image
42 Second image
43 Partial region
44 Corresponding region
45 Synthetic image (third image)

The invention claimed is:

1. A spectacle wearing parameter measurement device used in measurement of a spectacle wearing parameter of a subject who is to wear a spectacle frame, the spectacle wearing parameter measurement device comprising:
an information processing unit that acquires each of a first image as a face image of the subject in a spectacle-frame wearing state and a second image as a face image in a spectacle-frame non-wearing state and prepares a third image obtained by associating the first image and the second image;
a display screen unit that displays the third image prepared by the information processing unit;
an operation unit that specifies a measurement reference point of the spectacle wearing parameter on the third image displayed on the display screen unit; and
a computation unit that calculates the spectacle wearing parameter by using data of the specified measurement reference point.

2. The spectacle wearing parameter measurement device according to claim 1, wherein
the third image is a synthetic image obtained by synthesizing the first image in the spectacle-frame wearing state and the second image in the spectacle-frame non-wearing state and includes at least a measurement position.

3. The spectacle wearing parameter measurement device according to claim 2, wherein
the synthetic image is a synthetic image of a partial region of the first image in the spectacle-frame wearing state and a corresponding region of the second image in the spectacle-frame non-wearing state.

4. The spectacle wearing parameter measurement device according to claim 3, wherein
the partial region is a region including a rim part of the spectacle frame worn by the subject on the first image obtained by imaging a lateral side of the face of the subject, and
the corresponding region is a region not including an eyeball corneal part of the subject on the second image obtained by imaging a lateral side of the face of the subject.

5. A spectacle wearing parameter measurement program that causes a computer provided with a display screen unit and an operation unit and used in measurement of a spectacle wearing parameter of a subject who is to wear a spectacle frame to function as:
an image processing section that prepares a third image obtained by associating a first image as a face image of the subject in a spectacle-frame wearing state and a second image as a face image in a spectacle-frame non-wearing state;
a display control section that displays the third image by the display screen unit, the third image prepared by the image processing section;
an operation control section that causes the operation unit to specify a measurement reference point of the spectacle wearing parameter on the third image displayed on the display screen unit; and
a measurement computation section that calculates the spectacle wearing parameter by using data of the specified measurement reference point.

6. A position specifying method for specifying, when a spectacle wearing parameter about a subject is to be measured by using a face image of the subject in a wearing state of a spectacle frame, a measurement reference point on the face image required for the measurement, the position specifying method comprising:
acquiring each of a first image as the face image of the subject in a spectacle-frame wearing state and a second image as the face image in a spectacle-frame non-wearing state;
when the measurement reference point is to be specified, preparing and displaying a third image obtained by associating the first image in the spectacle-frame wearing state and the second image in the spectacle-frame non-wearing state; and
specifying the measurement reference point of the spectacle wearing parameter on the third image.

* * * * *